United States Patent
Morganroth

(10) Patent No.: US 6,708,057 B2
(45) Date of Patent: Mar. 16, 2004

(54) METHOD AND SYSTEM FOR PROCESSING ELECTROCARDIOGRAMS

(75) Inventor: Joel Morganroth, Gladwyne, PA (US)

(73) Assignee: eResearchTechnology, Inc., Philadelphia, PA (US)

(*) Notice: Subject to any disclaimer, the term of this patent is extended or adjusted under 35 U.S.C. 154(b) by 0 days.

(21) Appl. No.: 10/045,843

(22) Filed: Jan. 10, 2002

(65) Prior Publication Data

US 2003/0097077 A1 May 22, 2003

Related U.S. Application Data

(60) Provisional application No. 60/331,839, filed on Nov. 20, 2001.

(51) Int. Cl.$^7$ ............................. A61B 5/04; A61B 5/044
(52) U.S. Cl. ........................................ 600/509; 600/523
(58) Field of Search ................................ 600/509, 515, 600/516, 523, 525; 128/903; 607/32, 60

(56) References Cited

U.S. PATENT DOCUMENTS

| | | | | |
|---|---|---|---|---|
| 5,469,858 A | * | 11/1995 | Osborne | 128/710 |
| 5,515,176 A | * | 5/1996 | Galen et al. | 358/403 |
| 5,605,158 A | * | 2/1997 | Snell | 128/696 |
| 5,724,985 A | * | 3/1998 | Snell et al. | 607/30 |
| 5,891,049 A | * | 4/1999 | Cyrus et al. | 600/523 |
| 6,141,584 A | * | 10/2000 | Rockwwell et al. | 607/5 |
| 6,325,756 B1 | * | 12/2001 | Webb et al. | 600/300 |
| 6,575,901 B2 | * | 6/2003 | Stoycos et al. | 600/300 |

* cited by examiner

Primary Examiner—Carl Layno
(74) Attorney, Agent, or Firm—Duane Morris LLP

(57) ABSTRACT

In a method and system for processing an electrocardiogram (ECG), digital ECG data are received. The digital ECG data evinces a plurality of a patient's heartbeats detected during an ECG. Digital annotation data are generated representing marking to be shown on an ECG tracing of the plurality of heartbeats. An annotated ECG tracing image is produced using the digital ECG data and the digital annotation data.

56 Claims, 9 Drawing Sheets

FIG. 7

METHOD AND SYSTEM FOR PROCESSING ELECTROCARDIOGRAMS

FIELD OF THE INVENTION

This invention relates to methods and systems for processing electrocardiograms, and more particularly to methods and systems for collecting and interpreting electrocardiograms developed during clinical trials.

BACKGROUND OF THE INVENTION

Over the past several years, the United States Food and Drug Administration (FDA.) and the United Kingdom regulatory authority (CPMP) have recommended that all new drugs have electrocardiogram (ECG) testing to determine any effects of the new agent on humans, particularly the effects on the QTc interval of a patient's ECG. Several companies support these clinical trials by serving as centralized collection and interpretation points or laboratories for the handling, analysis and data reporting of these ECGs (hereinafter referred to as "processing companies"). Most processing companies rely on ECG machines programmed with algorithms for measuring the important ECG intervals (such as the heart rate, PR, QRS, QT and QTc durations), and a cardiologist later reviews the intervals and interprets the ECG's morphology. Reliance on ECG machines for determining interval duration leads to inconsistent and inaccurate results, intrinsically as well as between different machine programs. Further, ECG machines have difficulty identifying low frequency waves, leading to false positive and false negative readings, especially with respect to the QT intervals.

For several years, the assignee of the present application—eResearchTechnology, Inc. (eRT) of Philadelphia, Pa.—has been in the business of supporting clinical drug trials by providing centralized collection and interpretation of ECG services. The assignee, however, does not rely upon ECG machine measurements in measuring ECG intervals, but instead uses manual measurement techniques. This practice, although very accurate and reliable, further complicates the already cumbersome and paper-intensive process of generating regulatory-grade research data from ECG tracings for a sponsor of a clinical trial (i.e., data that are supported by an audit trail and are 100% verifiable by a government agency such as the FDA). An overview of this process is provided hereafter.

A sponsor, such as a pharmaceutical company, conducts clinical trials that typically include patients throughout the world. Each patient in a trial normally undergoes a series of ECG tests conducted during a series of visits to a study site (e.g., a doctor's office or hospital). The visits generally must occur during time periods specified by the sponsor in the research protocol. At several of these visits, an ECG machine is used to perform an ECG test and an ECG tracing is produced. The site collects ECG tracings from several patients in the clinical trial and forwards the ECG tracings to eRT, along with demographic data associated with each ECG. The demographic data usually include information such as a patient identifier, a study site identifier, the date of the test, the time of the test, a clinical trial identifier, the drug being tested, and the visit number for the patient (e.g., baseline, first visit, second visit, etc.). The demographic data are generally recorded on a label attached to the ECG reading. Alternatively, the demographic data and the ECG tracing are sent to eRT via electronic communications through a telephone network. In this alternative, the tracing and demographic data are then printed by eRT for later processing.

Once an ECG tracing is received, a source processing department manually enters the demographic information into a computer database via a computer and through a standard data entry screen. The screen is generic for all trials handled by eRT and, therefore, often includes data entry windows or areas that are extraneous and not pertinent to a particular trial. After the data are saved to a database, it must be confirmed that there have been no data entry mistakes. If a mistake is noted on the demographic information on the label, for example the patient's age was entered incorrectly on the label, or if a piece of demographic information is missing from the label, then a regulatory grade query must be conducted and documented. A query is forwarded to the query resolution department in the form of a paper copy of the ECG along with a note indicating the required query. A member of the query resolution department then telephones a study site or a site investigator associated with the study site to try to resolve any discrepancy or obtain any missing information from the demographic data. Telephone logs are maintained, and corrections are made directly onto the source document (the combined ECG and demographic label), initialed and dated. While the query resolution team conducts queries, the source document must be kept within the interpretation process so that the process can continue in parallel with the query resolution process; hence, copies of the source document are provided to the query resolution team.

A file associated with the ECG tracing is then forwarded to a diagnostic specialist. The diagnostic specialist verifies the analysis requirements of the clinical trial from a protocol book. The protocol book includes the analysis requirements and any updates to these requirements for each clinical trial supported by eRT. Analysis requirements typically include information identifying how many heartbeats must be measured for QT intervals per individual ECG tracing and permissible time periods when patient visits may occur.

The diagnostic specialist typically identifies the heartbeats that are to be measured with pen marks placed on each individual ECG tracing. The ECG tracing is then mounted on a magnetic board, and intervals are measured. A pointer device is placed on top of the ECG tracing. A first edge of an interval is visually identified using the assistance of a magnifying glass, and the pointer device is aligned over the first edge. A button is then depressed on the device, and a data point is registered with a dedicated, stand-alone computer connected to the pointer device. A second edge of the interval being measured is then identified in a like manner, and a second data point is registered. This process is typically repeated for PR, QRS, RR, QTc and QT intervals in order to compile separate interval duration measurements (IDMs) associated with at least three heartbeats. The interval data are then saved to the stand-alone computer, and the interval data are then transferred to a central computer server. A work sheet identifying a calculated mean of the measurement data for each interval is then printed and attached to the ECG tracing in its file. The diagnostic specialist then sorts worksheets and ECG tracings for the assigned cardiologist's review. If an ECG tracing is somehow separated from its file, the ECG tracing and worksheet are placed in a "return to file" bin. Any ECG tracings and worksheets in the "return to file" bin are then matched with the appropriate file by a member of the source processing team.

Once an ECG and its associated worksheet are placed in the correct file, the diagnostic specialist forwards the file to the assigned cardiologist for review. The cardiologist reviews the ECG and completes the worksheet. The cardiologist indicates his or her medical interpretation of the measured intervals and the ECG morphology on the worksheet. Some studies require the cardiologists to also review ECG tracings from prior patient visits and a baseline visit along with the current ECG tracing being evaluated. Satisfying this preference requires the physical retrieval of files from a filing system and the concomitant local storage of hardcopy files throughout the duration of a clinical trial.

Some of the ECG tracings are then forwarded to the quality control department based upon predetermined quality control criteria. For example, every ECG tracing associated with a worksheet that indicates that an abnormal interval is present is sent to quality control for review. These files are identified for the quality control department with POST-IT notes, produced by 3M Corp., affixed to each file. Also, 5% of all other ECG tracings are pulled for quality control. Additionally, a member of the quality control team telephones a sponsor, or a member of the source processing team faxes a sponsor, when certain criteria are met, e.g., a measured QT interval for an individual ECG tracing falls within a predefined dangerous range.

After an ECG has been quality controlled or passed over for quality control, a member of the source processing group faxes a preliminary reporting of the cardiologist's evaluation to the study site and/or the sponsor, as dictated by the trial protocol. The source processing department then sorts the worksheets and ECG tracings for data entry. The cardiologist's comments and analysis from each worksheet are entered into a database by a source processing member. Source processing then prints a final report and clips it to the worksheet and ECG tracing. The query resolution department then quality controls the data entry on the final report. Next, source processing photocopies the final report for the site and the sponsor. The final report is then sent to the site or sponsor by Federal Express or other courier according to the protocol for the clinical trial. This reporting is typically accomplished approximately ten days after the initial facsimile reporting. Source processing then files the patient's file on-site. All of the files associated with a clinical trial are archived at the end of a clinical trial.

It should be apparent from the above description that the current collection, interpretation and reporting process is very paper and task intensive. While the process ultimately produces regulatory-grade research data, there remains a need for an improved method and system that increases the efficiency and flexibility of the collection, interpretation and reporting process while generating regulatory-grade research data that is supported by an audit trail.

SUMMARY OF THE INVENTION

In a method and system for processing an electrocardiogram (ECG), digital ECG data are received. The digital ECG data evince a plurality of a patient's heartbeats detected during an ECG. Digital annotation data are generated representing markings to be shown on an ECG tracing of the plurality of heartbeats. An annotated ECG tracing image is produced using the digital ECG data and the digital annotation data.

The above and other features of the present invention will be better understood from the following detailed description of the preferred embodiments of the invention that is provided in connection with the accompanying drawings.

BRIEF DESCRIPTION OF THE DRAWINGS

The accompanying drawings illustrate preferred embodiments of the invention as well as other information pertinent to the disclosure, in which:

FIG. 7 is an example of an exemplary cardiologist graphical user interface;

DETAILED DESCRIPTION OF THE INVENTION

The Internet is a worldwide system of computer networks—a network of networks in which a user at one computer can obtain information from any other computer and communicate with users of other computers. The most widely used part of the Internet is the World Wide Web (often-abbreviated "WWW" or called "the Web"). One of the most outstanding features of the Web is its use of hypertext, which is a method of cross-referencing. In most Web sites, certain words or phrases appear in text of a different color than the surrounding text. This text is often also underlined. Sometimes, there are buttons, images or portions of images that are "clickable." Using the Web provides access to millions of pages of information. Web "surfing" is done with a Web browser; the most popular of which presently are Netscape Navigator and Microsoft Internet Explorer. The appearance of a particular website may vary slightly depending on the particular browser used. Recent versions of browsers have "plug-ins," which provide animation, virtual reality, sound and music.

Figure 1:
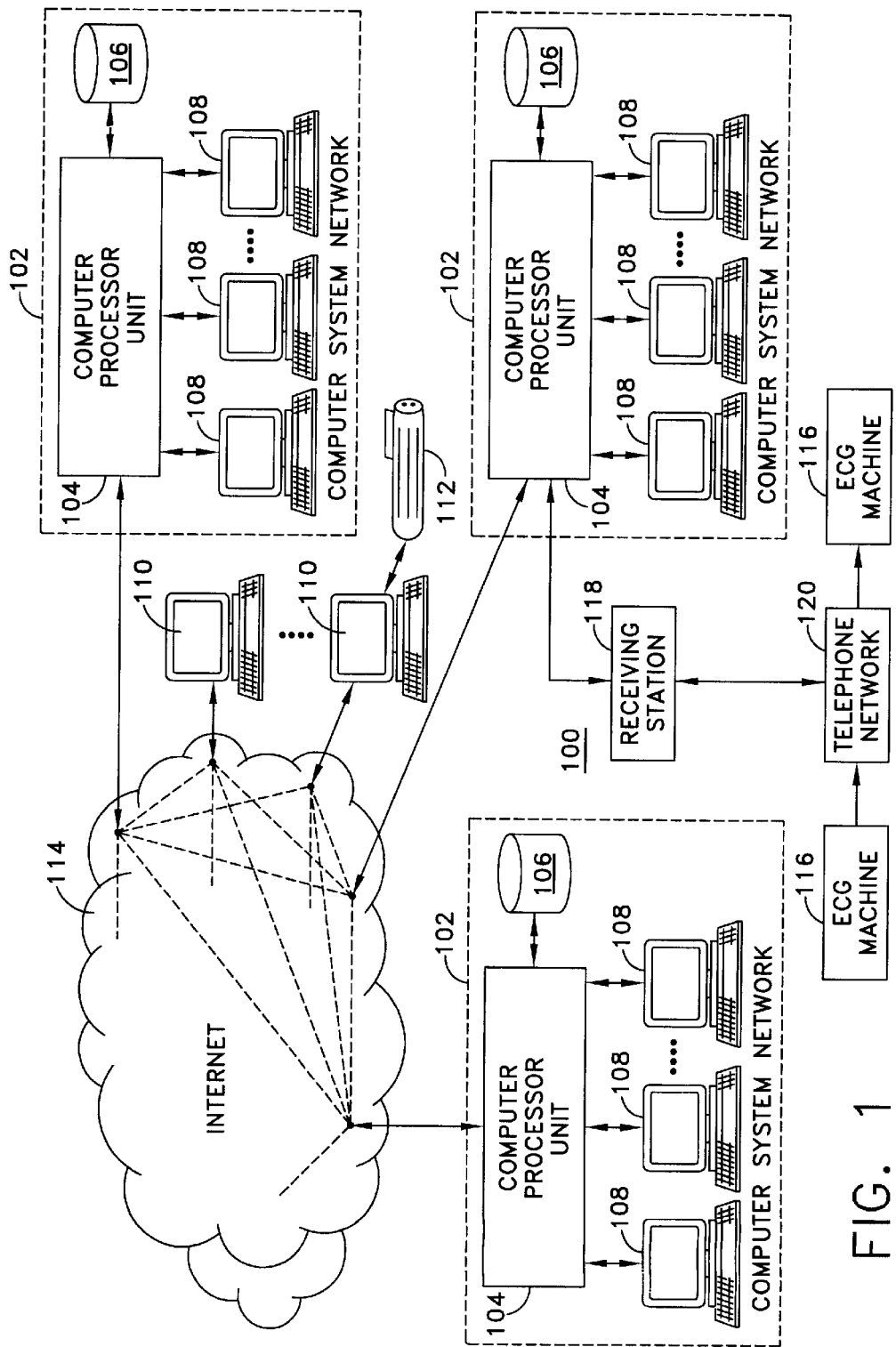
FIG. 1 is a stylized overview of a system of interconnected computer networks.

FIG. 1 shows a system 100 of interconnected computer system networks 102. Each computer system network 102 contains a corresponding local computer processor unit 104, which is coupled to a corresponding local data storage unit 106, and local network user terminals 108. A computer system network 102 may be a local area network (LAN) or part of a wide area network (WAN), for example. The local computer processor units 104 are selectively coupled to a plurality of user devices 110 through Internet 114 described above. Each of the plurality of user devices 110 and local user terminals 108 may have various devices connected to their local computer systems, such as scanners, barcode readers, printers, finger print scanners, mouse devices and other interface devices 112.

A user device 110, programmed with a Web browser or other software, locates and selects (such as by clicking with a mouse device) a particular Web page, the content of which is located on the local data storage unit 106 of a computer system network 102, in order to access the content of the Web page and the services provided therethrough. The Web page may contain links to other computer systems and other Web pages.

The user device 110 may be a microprocessor-based computer terminal, a pager that can communicate through the Internet using the Internet Protocol (IP), a Kiosk with Internet access, a connected personal digital assistant or PDA (e.g., a PALM device manufactured by Palm, Inc.) or other device capable of interactive network communications, such as an electronic personal planner. User device 110 may also be a wireless device, such as a hand-held unit (e.g., cellular telephone) that connects to and communicates through the Internet using the wireless access protocol (WAP).

The system and method of the present invention may be implemented by utilizing at least a part of the system 100 described above in connection with FIG. 1. It should be apparent to one of ordinary skill that the system may be incorporated in a LAN, in a WAN, or through an Internet 114 based approach, such as through a hosted or non-hosted application service, or through a combination thereof. The functionality of the method may be programmed and executed by a computer processor unit 104, with necessary data and graphical interface pages as described hereafter stored in and retrieved from a data storage unit 106. A user can access this functionality using a user device 110 or user terminal 108.

The functionality of the electrocardiogram (ECG) processing system and method are described hereafter with the aid of functional blocks. It should be understood that each functional block may be a program module that directs a computer processor unit 104 and/or terminal 108, 110 to perform specific functions. In one embodiment, this functionality is programmed in a computer processor unit 104 and is accessed via a terminal 108 and 110, either through the Internet 114 or through local computer network 102.

Figure 2:
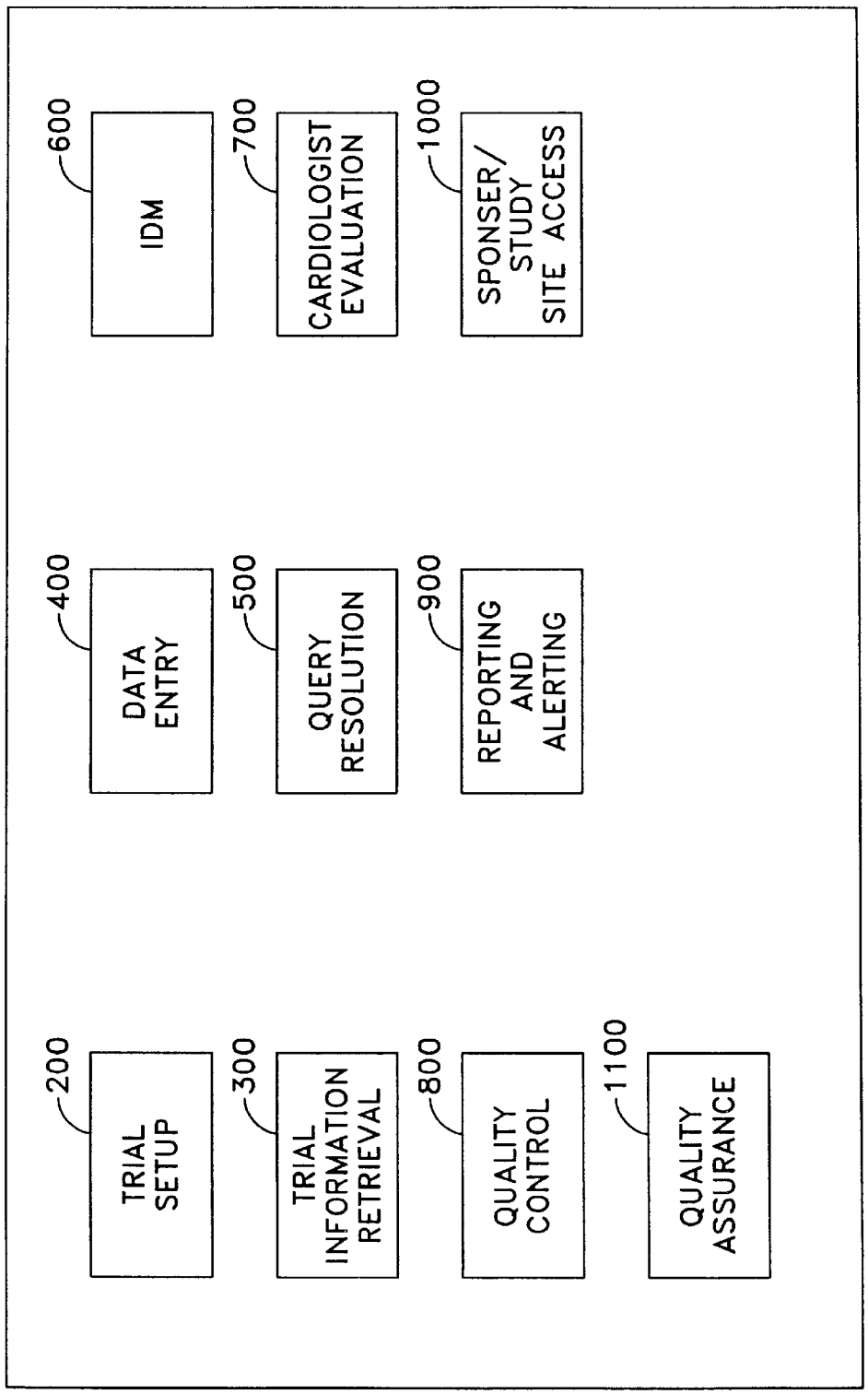
FIG. 2 is a block diagram illustrating exemplary functional software modules of the present invention.
Figure 3:
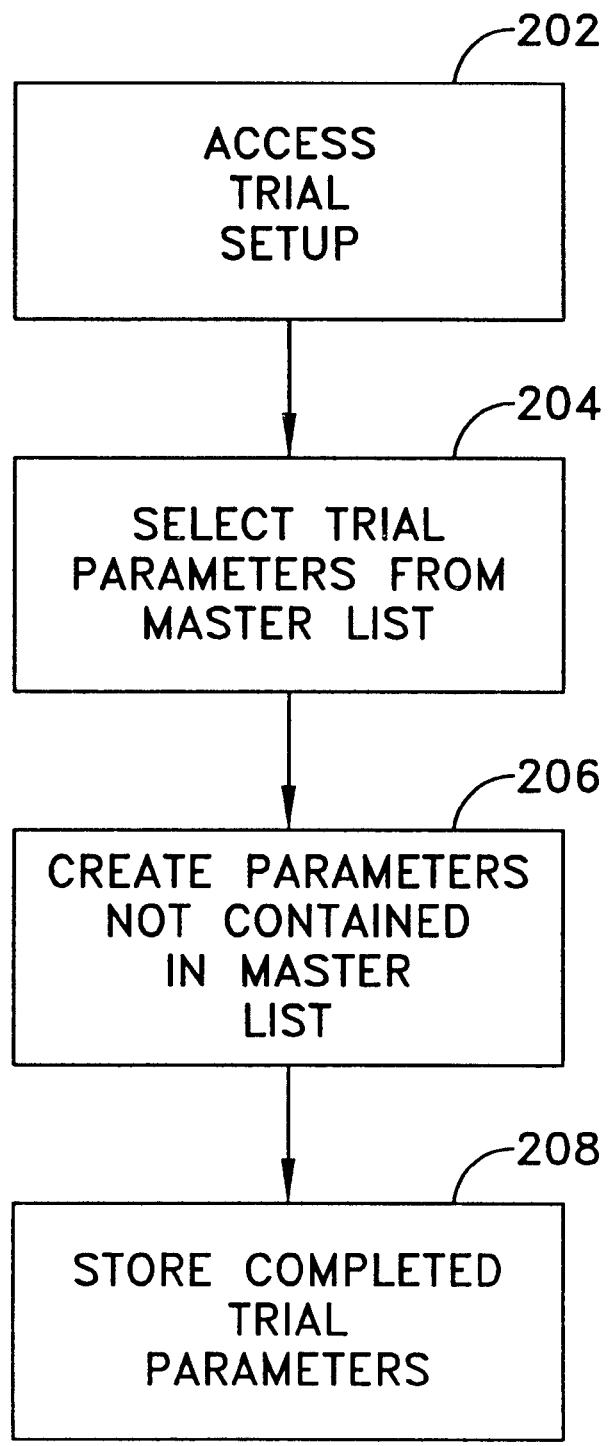
FIG. 3 is a flow diagram illustrating an exemplary Trial Setup module.

FIG. 2 illustrates in block form exemplary program modules of the processing system 100. Trial Setup module 200 of FIG. 2 is utilized to set the necessary parameters of each trial that is supported by the system. At 202 of FIG. 3, the Trial Setup module 200 is accessed using a terminal 108 or 110. Access to this module should be limited to authorized personnel in order to ensure that setup of initial trial parameters and all modifications to established trial parameters are authorized. Access may be restricted in any conventional manner, such as through requiring a username and password to gain access.

Trial parameters preferably are selected at 204 from a master list of parameters. The trial parameters represent data that must be collected pertaining to each processed ECG tracing within a specific clinical trial and the governing protocol and rules for the clinical trial. Examples of data that may be collected relative to each ECG within a trial include patient identifier, patient ethnicity, patient gender, patient date of birth, trial identifier, visitation date, time and number, study site identifier, etc. (collectively referred to herein as "demographic data"). Graphical interfaces created by the system for interacting with users are customized according to the parameters established at step 204. For example, if particular data are not required for a trial, a data entry graphical interface generated by Data Entry module 400 of the system does not prompt a user to enter that data. The interface is also preferably customized, for example, as to the format of the data to be entered, e.g., the number of characters that a sponsor uses in a trial identifier or patient identifier and the like. This feature increases the speed, efficiency and accuracy of the data entry process and, therefore, facilitates the generation of regulatory grade data.

The governing protocol for the trial is also established at 204. The governing protocol includes the set of rules established by the trial sponsor (e.g., a pharmaceutical company) for the trial and the processing company and other information that generally pertains to the clinical trial (e.g., sponsor name, title of the trial, target population, etc.). Examples of protocol rules include requirements for site identifiers and patient identifiers (e.g., the format of the identifiers), total number of ECGs required per patient, time and date restrictions or requirements for patient visits and ECG tests, parameters to be measured for each ECG tracing (e.g., kinds of intervals to be measured and number of interval measurements), alarm conditions (e.g., specific measured interval duration ranges that trigger an emergency reporting to the study site and/or sponsor), evaluation conclusions to be provided by a cardiologist, and reporting methods and times, and query methods. Contact information is also provided for the sponsor, each participating study site, and each investigator associated with each participating study site. Contact information may include a person's name, address, telephone number, facsimile number, electronic mail address, preferred contact method, office hours, and the like. The module 200 may also be accessed after the initial setup process in order to modify or update any trial parameters that are changed by the sponsor during the course of a trial.

Any trial parameters that are not contained in the master list of trial parameters may be created or added at 206 using the module 200. These parameters may also be added to the master list if desired. After the trial parameters are established for a particular trial, the trial setup data are stored to data storage unit 106, e.g. an Oracle standard database, at 208. The clinical trial is essentially registered into the system, and ECGs associated with that trial may be accepted for processing in the system.

In an exemplary processing system, ECG tracings and related demographic data may be received from a study site in several manners. A hard copy of an ECG tracing may be mailed or otherwise forwarded from a study site to a processing company. Each ECG preferably has affixed thereto a data sticker that includes a barcode. The barcode preferably includes data identifying the trial and the study site. In an exemplary system, these barcodes are pre-printed by the ECG processing company and forwarded to the various study sites that are participating in a specific trial. The data entry sticker also preferably includes sufficient space for handwritten or typed entry of data required by the trial parameters and protocol, such as patient identifier, site identifier, date of birth of the patient, visit number, etc.

If a hard copy of the ECG tracing is received, the heartbeats associated intervals that are to be analyzed are identified by hand placed marks made on the ECG tracing by an analyst. Each protocol requires a specific number of heartbeats from an ECG tracing to be analyzed. If the analyst needs to identify or reconfirm the total number of intervals to be measured or the type of intervals to be measured, as dictated by the clinical trial, the analyst can access the Trial Information Retrieval module 300 and retrieve this information (entered through Trial Setup module 200) from a data storage unit 106. The analyst then identifies the heartbeats to be analyzed with, for example, a pen mark made above or below each selected heartbeat. Trial Information Retrieval module 300 provides access to the protocol parameters of a trial, as established in Trial Setup module 200. The Trial Information Retrieval module 300 is preferably searchable, thereby relieving the need for examination of a hardcopy protocol book.

An image of the marked hard copy is then entered into the system with a scanner device 112, and the image is stored in data storage unit 106 as digital ECG data. The barcode is also read with a barcode reader, and the image is correctly associated with the trial and study site identified by the data contained in the barcode. This information is also used to retrieve a graphical data entry interface, with Data Entry module 400, that is customized to the identified trial based upon the parameters entered with the Trial Setup module 200. The graphical data entry interface prompts a user to enter data dictated by these parameters. The data specialists visually reads data identified on the data sticker, and the data specialist enters the data into the data entry interface using a terminal 108 or 110 for storage in data storage unit 106. Additional details of the data entry process and Data Entry module 400 are provided below.

Alternatively, a digital ECG file is received via a network, such as the Internet 114 or a telephone network, in an appropriate file format. The digital ECG file may be received along with a data file including digital demographic data identifying, for example, the patient and the study site. The digital ECG file may include either an image of an ECG tracing (e.g., an image file such as a portable document format (PDF) file, a portable neutral graphics (PNG) file or a Bit Map (BMP) file) or digital data representative of an ECG waveform (e.g., data points evincing a plurality of a patient's heartbeats detected at at least one lead of an ECG). ECG tracing images can be generated from image files using plug-ins, such as ADOBE ACROBAT, WINDOWS Image Viewer, or other viewers. An ECG tracing can be generated from either type of digital file for printing. An analyst can then mark the heartbeats for analysis as described above. The tracing is then scanned into the system, and data entry proceeds using Data Entry module 400, if a demographic data file is not included. Alternatively, demographic data can be exported from any accompanying digital demographic data file and stored in database 106.

More preferably, though, when a digital ECG file is received (either an image file or a data point file), a software program as described below is utilized to create linked files that may be used to produce an annotated ECG tracing image on a display (e.g., a monitor) using the original and unmodified digital ECG file and an associated and linked digital annotation file including digital annotation data representing markings to be shown on an ECG tracing image evinced by the digital ECG data. Essentially, image overlays are created.

In one exemplary embodiment of the present system, digital ECG files are received from one or more ECG machines 116 at a receiving station 118. The receiving station 118 is a dedicated, stand-alone computer that includes proprietary software for receiving data files via modem communications from ECG machines 116 through telephone network 120. Each ECG machine 116 is made by a specific manufacturer, which typically develops its own receiving station 118 for communicating with its ECG machine 116. Examples of companies that provide ECG machines and corresponding receiving stations include Marquette Medical Systems (which provides the MUSE receiving system), Mortara (which provides the E-SCRIBE receiving station), and Card Guard (which provides the TELEMEDICINE receiving station). In this embodiment, the processor 104 includes code for directing the processor to export these data files from the receiving stations 118 into database 106. In one embodiment, this code is provided as an XML (extensible markup language) export file that exports digital data points for the ECG waveform and digital demographic data into database 106. This code may also be provided to export data in a HL-7 format, or any other format that might be required by the FDA or other regulatory agencies. An ECG waveform can then be generated on a monitor of a terminal 108 or 110 from data in the digital file.

A software program as discussed in connection with IDM module 600 within processor 104 and/or terminals 108, 110 enables on-screen measurement of intervals displayed on a display of a terminal 108, 110. The original digital ECG data and demographic data are preserved in the database of data storage unit 106. The program displays markings, such as marks indicating the intervals that are measured, actual interval duration measurement data, and interval endpoints, on an ECG image in an annotated ECG image. As described above, any such annotations that are to be shown on an ECG image generated from digital ECG data are recorded as digital annotation data in data storage unit 106 in a linked file, but the original digital ECG data remain unchanged in order to maintain the integrity of data for audit purposes.

Whenever data associated with an ECG tracing are entered into the system 100, the accuracy of the data must be confirmed. Accuracy of data, such as demographic data, is extremely important in clinical trials that are to be reviewed by an agency such as the FDA. All data entry is preferably accomplished via double data entry, as opposed to single data entry that requires manual quality control and editing as described in connection with the prior processing system. The Data Entry module 400 preferably prompts a data specialist to enter data a first time. After the data are entered, the Data Entry module 400 preferably prompts another specialist to enter the data a second time. The module 400 then compares the data entered the second time with the data entered the first time. If the data are identical, it is assumed that the data have been accurately entered. The data are then stored in data storage unit 106. Time and date stamp data are also preferably stored for each data entry session. If the data are not identical, the module prompts a specialist to enter the data a third and final time. The module also preferably alerts the data specialists when data for a required data category have not been entered. If the data specialists has simply forgotten to enter the data, the specialists can enter the data as indicated above. If the data are unavailable, e.g., the data are absent from the data sticker on the ECG tracing or are not included in the received digital demographic data, the data specialist flags the data as unavailable or missing with Data Entry module 400.

Figure 4:
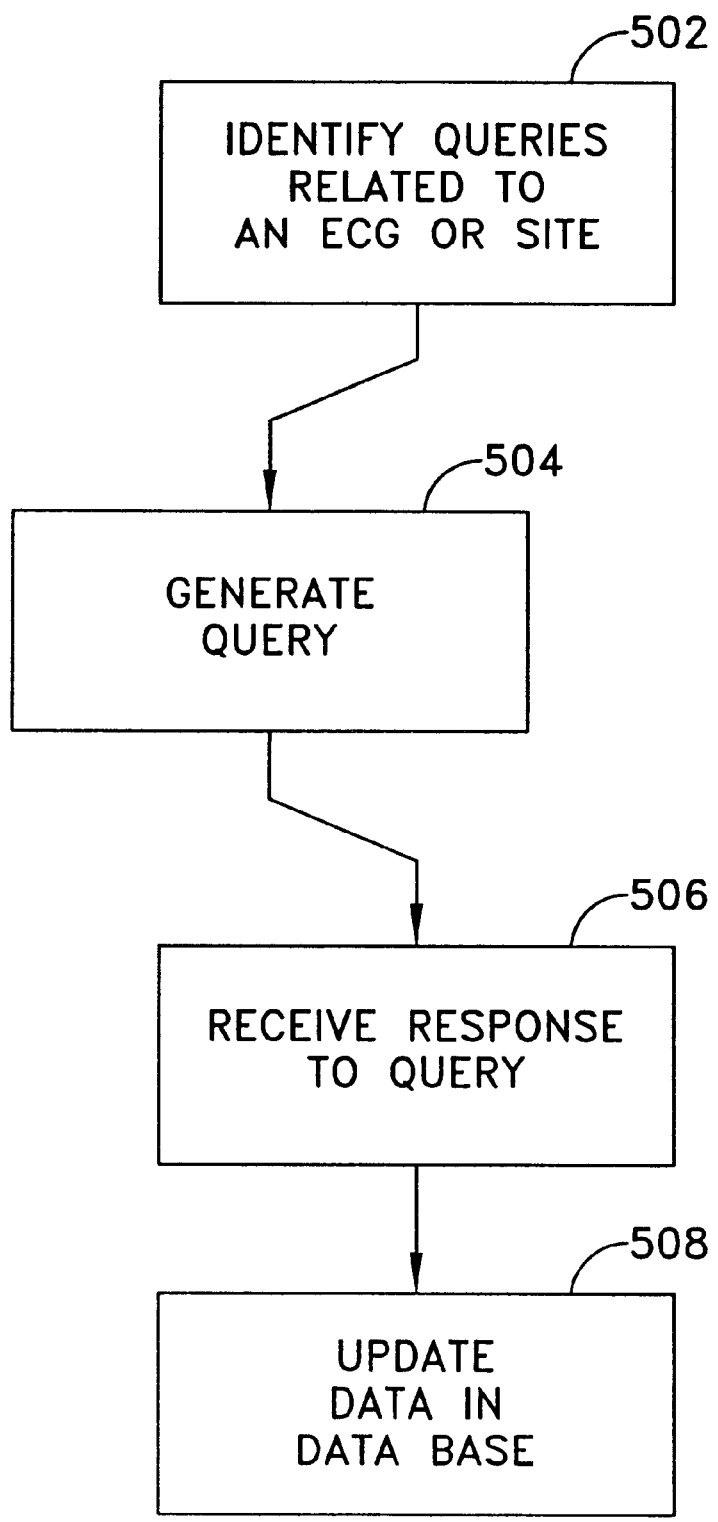
FIG. 4 is a flow diagram illustrating an exemplary Query Resolution module.

After data has been entered for an ECG tracing or group of ECG tracings (whether manually through Data Entry module 400 or as exported from a digital file), the Query Resolution module 500 reconciles any apparent data errors, absences, or inconsistencies using the digital parameter data provided via the Trial Setup module 200 and/or digital demographic data provided via the Data Entry module 400. Referring to step 502 of FIG. 4, the Query Resolution module 500 identifies data errors, absences or inconsistencies based upon the demographic data and/or parameter data. For example, if data, such as the age of a patient, are "unavailable" as indicated above, the Query Resolution module 500 automatically generates an electronic mail query, a facsimile query or a postal query at 504 to a contact identified for the study site and trial associated with the ECG tracing. This contact information, such as the name of a doctor, administrator, or investigator associated with the trial and the study site, and address information, e.g., postal address, electronic mail address or facsimile number, are preferably provided as trial parameter data to the Trial Setup module 200 in the trial setup process of FIG. 3 and are retrieved from database 106. Of course, if a postal query is to be sent to the contact, the system may alert a query resolution specialist of the processing company by electronic mail, for example, or through a query queue accessible to the specialist when the specialist logs into the system, so that the specialist is alerted to send the postal query to the identified contact. Regardless of the query method, a query resolution specialist is preferably alerted by the Query Resolution module 500 each time a query is sent. The preferred query method (e.g., electronic mail, facsimile or postal) is also identified during the trial setup process using Trial Setup module 200.

Data errors and inconsistencies are also identified for query resolution at 502. For example, demographic data identifying a patient visit date may be entered for a date that precedes the beginning date of the associated trial, as identified from the parameter data. Because the date was likely entered into the system correctly (because of the double data entry feature), it may be assumed that the date was entered incorrectly on the data sticker attached to the ECG tracing at the study site or in the digital demographic data received by computer processor unit 104. A query may then be sent to the site in order to identify the correct date. In another example, multiple ECG tracings may be processed for the same patient within the same trial. Patients are typically identified by a patient identification number. If data associated with a first ECG for the patient identification number indicate that the patient is male and data for a second ECG indicate that the patient is female, this inconsistency in the demographic data can be resolved via a query generated by the Query Resolution module 500 at 504. In still another example, if demographic data entered for an ECG indicate that the ECG was taken during the patient's third visit, the query resolution module 500 generates an appropriate query if it is identified at 502, for example, that no ECG has been received and processed for the second patient visit and no demographic data has been entered for the second visit. The query is directed to resolving whether the demographic data identifying the visit as the third visit are incorrect (i.e., the visit was actually the second visit) or whether the ECG data and demographic data for the second patient visit have not been received.

Responses to queries are received at 506 in the form of return electronic mails, facsimiles, postal correspondence, or telephone calls placed to a query resolution specialist of the processing company. The system preferably does not automatically update the data in the database of data storage unit 106 with resolution data that it receives (such as by electronic mail), but rather, a query resolution specialist preferably examines the response data and enters the data and updates the data in the database 106 based upon the response. This step allows for the generation of an audit trail for the modified or supplemented data. For example, when data associated with an ECG tracing are modified by a specialist based upon a query response, the Query Resolution module 500 preferably requires the query resolution specialist to enter his or her initials and a date of the change or affix an electronic signature, as discussed below. The specialist also preferably updates the status of the query in the system as "resolved."

As indicated at 502, the Query Resolution module 500 may also identify queries related to a study site, a trial, an investigation, or other query related parameter. A query identification routine may be run periodically, such as weekly or monthly, for example. All outstanding queries for a single study site identified by the query identification routine can then be forwarded together to the correct contact at the site. Alternatively, each time a query is identified for a study site, the Query Resolution module 500 can identify all queries for the site having a status that is "unresolved." The module can then generate reminder queries along with the new query.

The Query Resolution module 500 may also be used to generate query status reports. This function may be performed periodically as programmed or be manually initiated by a query specialist. For example, status reports for queries identifying the type of query, query date and status can be generated based upon an investigator, a study site, a doctor, a trial, a specific time period, a query type or any combination thereof.

An ECG tracing is preferably not released for further processing unless all outstanding queries have been resolved, as indicated by the Query Resolution module 500. If a query cannot be resolved satisfactorily, e.g., the resolved ECG date does not fall within the date limits of the trial and, therefore, violates a rule of the clinical trial or the information is not available, the ECG tracing is preferably flagged as such after the query resolution process. The ECG is withheld from processing within the clinical trial until some form of query resolution occurs. Even if the ECG is flagged as violating trial rules, however, it is still preferably processed after query resolution to evaluate whether the ECG reveals any abnormalities.

After an ECG tracing is released for further processing, i.e., it was the subject of no queries or all outstanding queries have been resolved, the ECG tracing is ready for interval duration measurement (IDM), e.g., measurement of PR, QR, QT, QTc, RR, and/or QRS intervals. Each ECG is preferably identified in a queue and may be assigned to a specific diagnostic specialists. This assignment may be made based upon protocol rules or parameters established with the Trial Setup module 200 or be based upon availability of the diagnostic specialist. The queue may also list a priority level for each ECG, e.g., "Stat" for high priority. This priority level may be set during the data entry process or be set automatically by the system based on a schedule or deadline rule entered with the Trial Setup module 200. The diagnostic specialist accesses the queue of ECGs using the IDM module 600 and selects an ECG from the queue for measurement.

The diagnostic specialist can measure intervals by the magnetic board method described in the background section. Of course, for this measurement method, the original paper copy of the marked tracing or a copy of the image must be used. Alternatively, if an ECG file is received as a digital file including digital ECG data evincing a plurality of heartbeats of a patient detected during an ECG test, or if an ECG is received as paper that is scanned to create a digital image file, the same measurements may be generated using images displayed on a monitor of a terminal 108 or 110. A calibration line generated on the monitor of a terminal is controlled by a pointer device, such as a mouse and is moved to identify interval edges. Data points identifying interval edges are generated when the pointer device is "clicked" or triggered. In either case, interval duration data associated with each heartbeat are developed and stored in database 106 for each ECG. The duration data and the annotation data (such as marks identifying specific heartbeats or intervals, marks showing duration data, and/or marks indicating interval endpoints) are saved as digital measurement data and digital annotation data, respectively. The original digital files (whether they be image files or data point files) are not modified in order to show an annotated ECG image on a monitor. Rather, files including the annotations are linked to the original digital ECG data, thereby preserving the integrity of the original data. Further, the annotations enable an agency such as the FDA to identify exactly what points on the ECG waveforms where used to take the measurements. In an exemplary embodiment, software that provides the measurement and annotation data features is developed from the CALECG software product provided by A.M.P.S., LLC of New York, N.Y. The terminal 108 or 110 used to perform and record these measurements is preferably networked as shown in FIG. 1, such that access to a common database 106 of the system is provided and access to the functionality of the other modules described herein is also provided.

Figure 5:
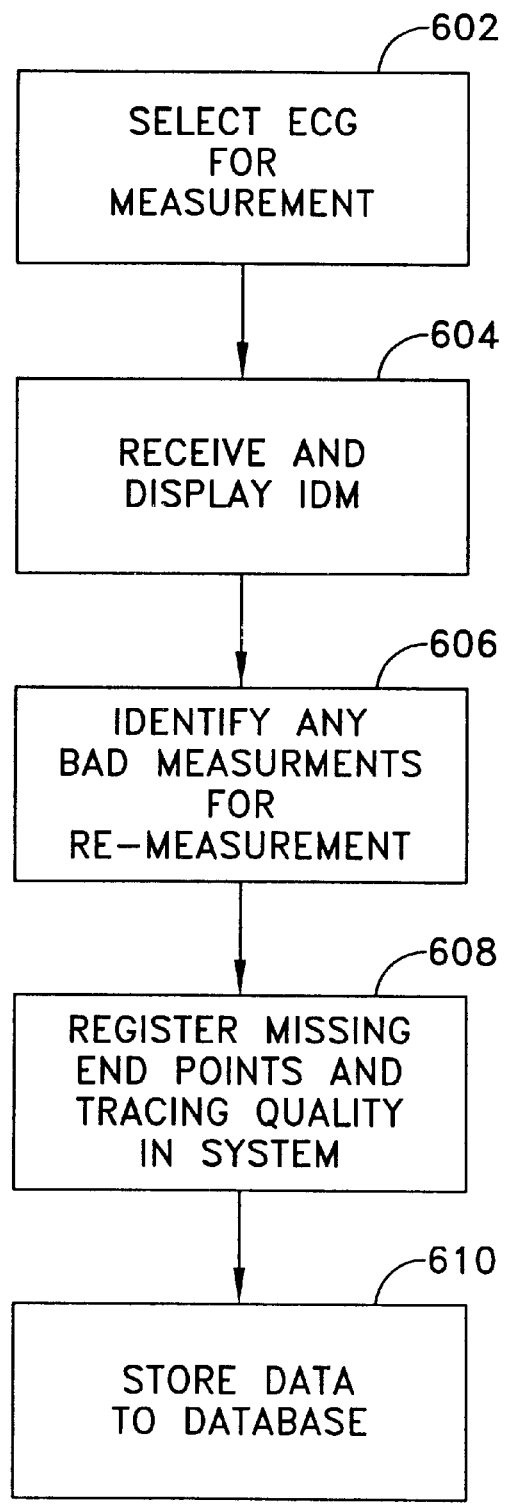
FIG. 5 is a flow diagram illustrating an exemplary interval duration measurement (IDM) module.

FIG. 5 illustrates a flow chart of the functionality of the IDM module 600. At 602, an ECG is selected by a diagnostic specialist from the queue as described above, and at 604, interval durations are measured. The interval duration for a measured heartbeat is preferably displayed to the specialist by a terminal 110 or 108 in connection with the annotated ECG image. The IDM module 600 examines the measured data for indications of bad or impossible measurements at 606 and prompts the specialist to re-measure an interval or group of intervals if a bad or impossible measurement flag is triggered. For example, a second edge of a first measured interval may not have properly registered prior to identifying the first edge of a second measured interval. An abnormally large interval is then recorded. Such an abnormally large interval measurement may trigger a re-measurement flag. At 608, identification of non-measured intervals and reasons therefor are registered in a graphical interface by the specialist. Reasons may include poor tracing quality or flat intervals, or lack of clear interval endpoints. The measurement data and any data entered at 608 are then stored in database 106 at 610 along with any digital annotation data (e.g., annotation data representing interval endpoints, measurement markings, etc.).

After a diagnostic specialist has measured the IDMs, the evaluation is eligible for quality review. Some of the ECGs are identified in the quality control queue of the Quality Control module 800 according to a predefined set of rules. For example, a particular percentage, such as 5%, of all ECGs may be selected for quality control. Also, any ECG associated with digital IDM data indicating an abnormal or a dangerous interval duration, based upon a predefined range of abnormal or dangerous interval durations, may be automatically selected for quality review. The intervals measured for the marked heartbeats of ECGs selected for quality control are reviewed by a quality control specialist and may be queued for remeaurement, if desired, prior to evaluation by a cardiologist.

After the interval measurements have been recorded into the system, the ECG is released to the queue of the cardiologist assigned to the ECG. A single cardiologist or small group of cardiologists is preferably assigned to a clinical trial in order to maintain optimal consistency in the ECG evaluation process, with an alternate cardiologist or alternates being assigned in case the first cardiologist or group of cardiologists is unavailable. The cardiologists and alternates may be assigned using the Trial Setup module 200. Each cardiologist registered in the system is assigned a queue that identifies any ECGs assigned to the respective cardiologist that are ready for evaluation, i.e., ECGs for which intervals have already been measured as described in connection with IDM module 600.

The cardiologist may access the processor 104 and database 106 through a local area network, a wide area network, or through the Internet 114. This feature allows remote viewing and evaluation of ECG tracings and interval data using a terminal 110, 108 remote from a processor 104 and database 106. This in turn allows for ECGs to be evaluated by cardiologists, who have appropriate security access, throughout the world and, therefore, in different time zones. Cardiologists can work from their homes or offices, and cardiologists from different areas of the world can be assigned to a single trial, thereby allowing evaluations to be prepared "around the clock."

Figure 6:
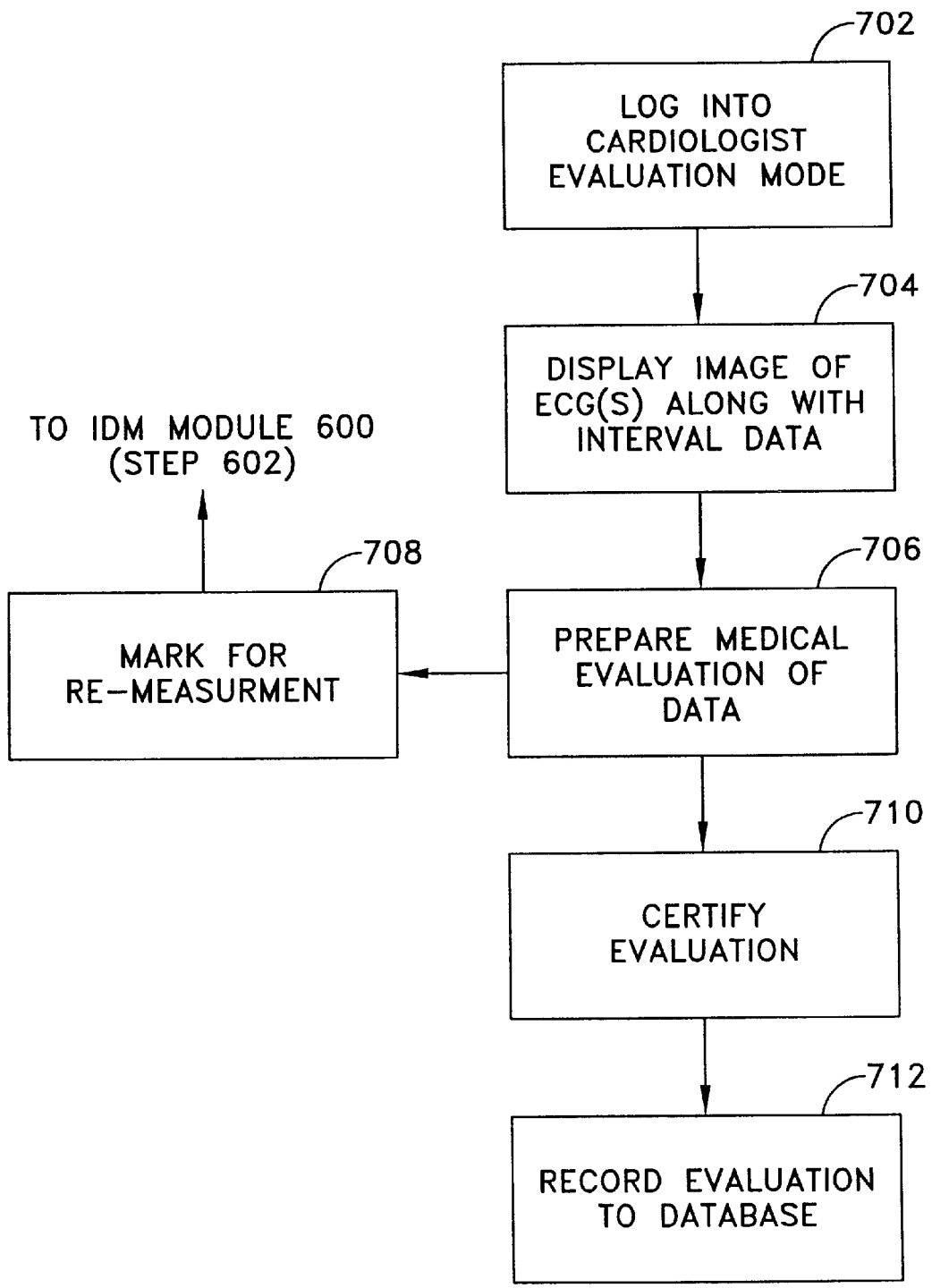
FIG. 6 is a flow diagram illustrating an exemplary Cardiologist Evaluation module.

FIG. 6 illustrates the functionality of the Cardiologist Evaluation module 700. At 702, the cardiologist logs into the Cardiologist Evaluation module 700, preferably using a username and password. At 704, the cardiologist selects an ECG for evaluation. The marked ECG image is retrieved from database 106 and is displayed to the cardiologist along with the measurement data described above. More specifically, an annotated ECG image is developed using the digital ECG data evincing a plurality of a patient's heartbeats detected during an ECG and the associated digital annotation data representing marking to be shown on an ECG tracing image of the plurality of heartbeats, unless the marked image is a scanned copy of a hand-marked ECG tracing.

Oftentimes, cardiologists prefer to examine ECGs of prior patient visits in conjunction with the ECG currently being evaluated. Assuming the cardiologist is examining an ECG taken during a patient's fourth study site visit during a trial, the cardiologist can retrieve the ECG images, measurement data, and evaluation data for visits one through three from database 106, as well as a baseline image and associated data. This feature greatly simplifies the evaluation process and allows for remote, paperless cardiological evaluations.

At 706, the cardiologist prepares a summary of his or her medical evaluation of the ECG and the interval measurement data reviewed by the cardiologist. The evaluation may be entered through an evaluation sheet graphical user interface that prompts the cardiologist to respond to specific questions dictated by the trial, such as whether the ECG is normal or abnormal and questions pertaining to heart rhythm, heart conduction, previous myocardial infarction, ST-T wave changes, presence of u waves, etc. The Cardiologist Evaluation module 700, while not providing medical evaluations of the ECGs, preferably checks that evaluation data provided by the cardiologist are consistent. For example, if the cardiologist indicates that a specific abnormality is present, the module 700 does not allow the cardiologist to release or certify an evaluation that also proclaims that the ECG is "normal."

If the cardiologist feels that the intervals that were marked for evaluation were not representative of the patient's heart rhythm or that a re-measurement should be taken for any reason, the cardiologist can digitally tag the ECG at 708 and note the heartbeats associated with intervals that should be measured. The ECG is then forwarded to or identified in a re-measurement queue of IDM module 600 and the measurement process continues as described above.

Figure 7:
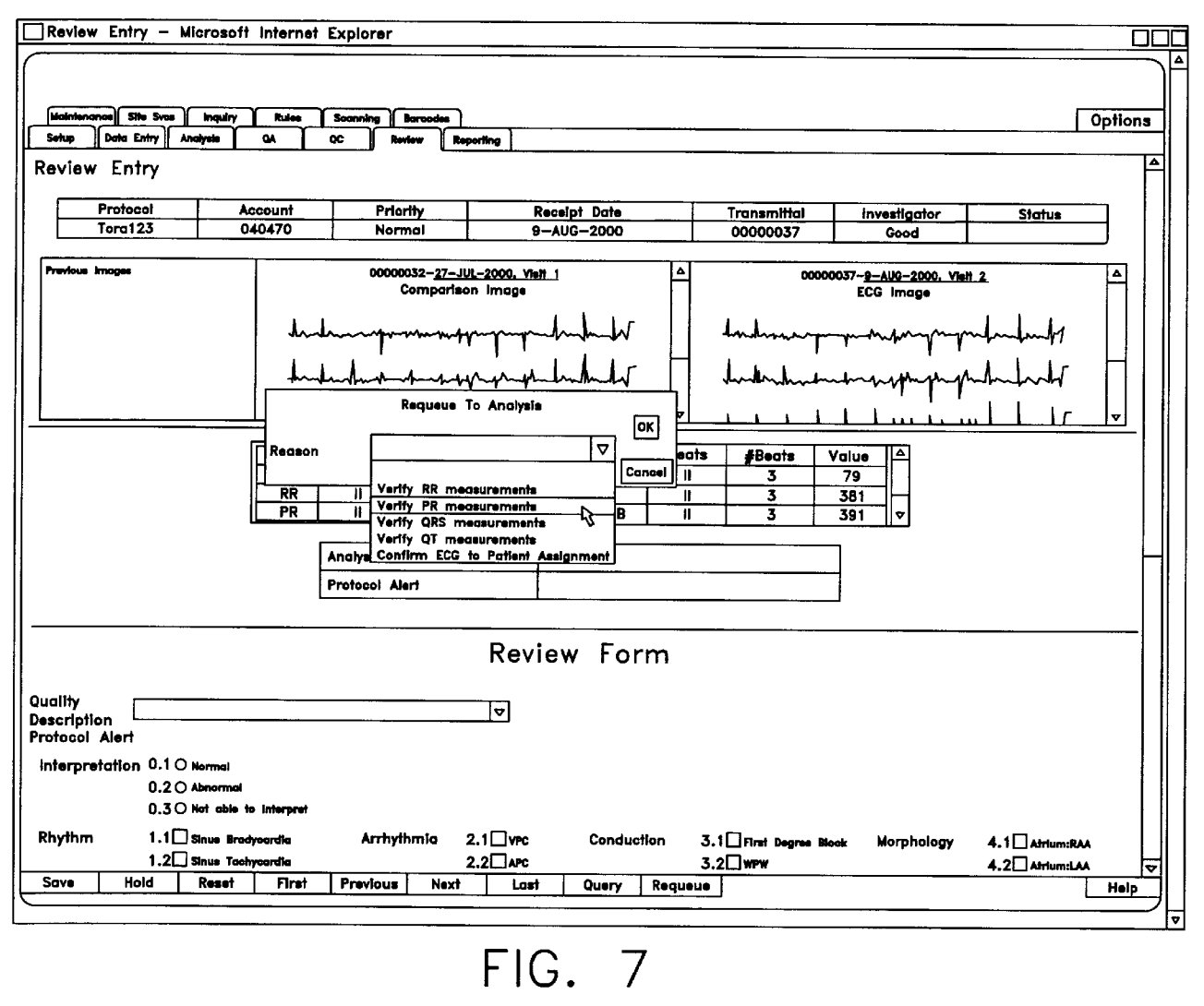

FIG. 7 illustrates one exemplary graphical user interface provided a terminal 110, 108 by the Cardiologist Evaluation module 700 for display to a cardiologist. As can be seen in the interface, the cardiologist can enter evaluation data by way of selectable options pertaining to the cardiologist's interpretation of the ECG and interval duration data ("normal", "abnormal" or "not able to interpret"), the heart rhythm, arrhythmia, conduction and morphology, ST-T wave changes, presence of u waves, etc. The interface of FIG. 7 also displays a "thumbnail" image of an annotated ECG image of the current ECG being evaluated—the ECG taken during a patient's second visit, for example,—and, if requested, at least one ECG image pertaining to a prior ECG—such as the patient's first visit. The interface allows the cardiologist to requeue the ECG being evaluated for remeasurement of specific intervals through the IDM module 600. For example, the cardiologist can request verification of the RR, PR, QRS, QTc or QT intervals or confirmation of ECG to patient assignment. The cardiologist can send the ECG back to the diagnostic specialist to remeasure the same beats through the IDM module 600, or the cardiologist can send the ECG to the Query Resolution module 500 if the cardiologist thinks that the ECG is not really from the patient identified by the ECG.

Figure 8:
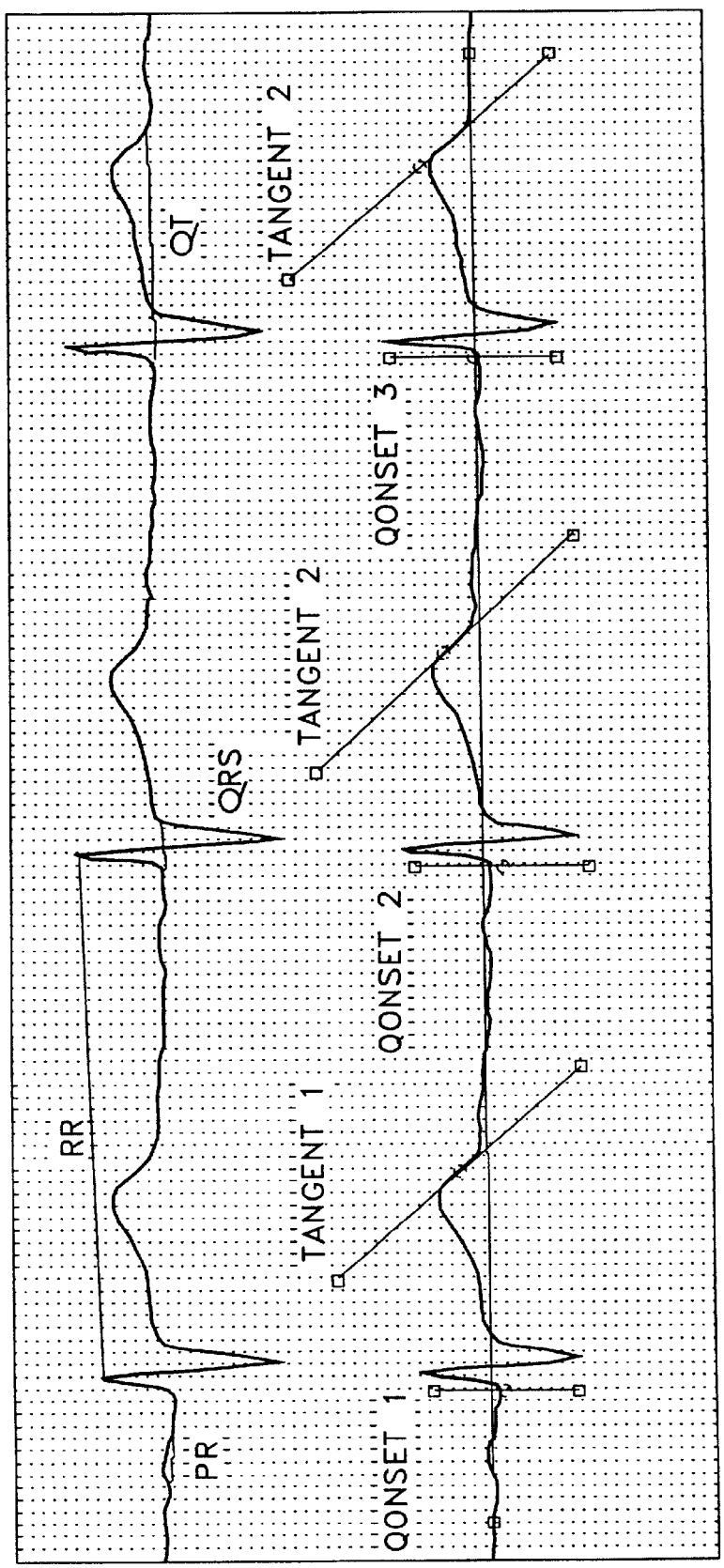
FIG. 8 is an example of an annotated ECG image.

By selecting one of the thumbnail images, the annotated ECG image is displayed to the cardiologist and is generated from digital ECG data and associated digital annotation data. For purposes of example not by way of limitation, FIG. 8 shows an ECG tracing displayed to a cardiologist evincing a heart rhythm detected by two leads of an ECG machine. Preferably, the cardiologist can view six to twelve leads at a time. Each lead tracing in FIG. 8 shows three heartbeats associated with various interval duration measurements made as described above. Several markings are shown on the image and are generated from digital annotation data associated with the various interval duration measurements. These markings pertain to, for example, measurement of the PR, RR, QRS, QTc and QT intervals as shown in FIG. 8. Actual interval measurement data (e.g., the measured time duration of an interval or intervals) may also be shown on the ECG tracing as markings or, alternatively, displayed to the cardiologist in an interface such as is shown in FIG. 7.

Figure 8A:
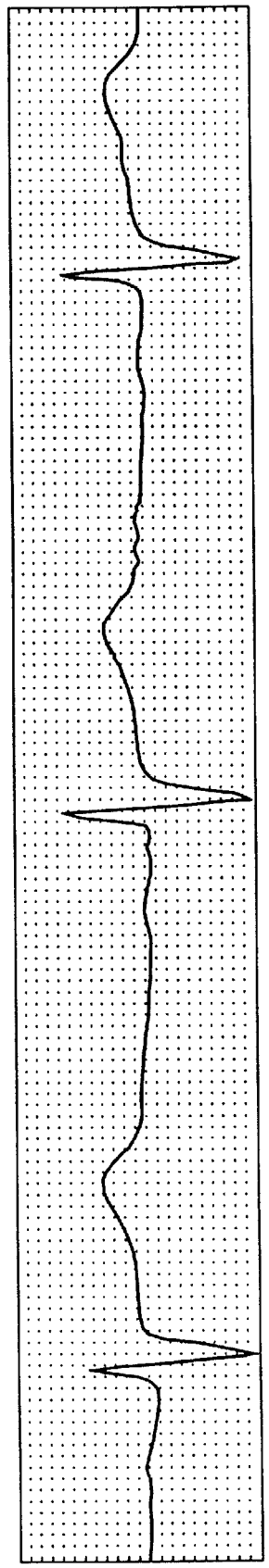
FIG. 8A illustrates the ECG image of FIG. 8 without annotation.

FIG. 8A illustrates an unannotated ECG image generated from the digital ECG data utilized in generating the annotated ECG image of FIG. 8. Such an unannotated ECG image may also be displayed to a cardiologist by the Cardiologist Evaluation module 700 if desired. A comparison of FIGS. 8 and 8A clearly shows the annotated markings displayed on the ECG image in FIG. 8.

After the cardiologist has entered his or her evaluation, the cardiologist preferably must certify the evaluation. Regulatory agencies generally require two forms of verification if verification is provided digitally and one form of verification if the signature is provided biometrically (e.g., a fingerprint). In the present system, a digital signature for the cardiologist is stored in database 106 and is affixed to the completed evaluation data sheet. A fingerprint (or thumbprint) reader may be connected to a cardiologist's terminal 108, 110 as a device 112. The terminal 108, 110 is also programmed with software for interfacing the terminal with the reader. An exemplary reader and accompanying software are available from, for example, from Digital Persona of Redwood City, Calif. The system reads the cardiologist's fingerprint or thumbprint using the reader. The print can be compared to a stored copy of the cardiologist's fingerprint or thumbprint in data storage unit 106, for example, in order to verify the cardiologist's identity. If a positive identification is made, the evaluation is certified, and the certified evaluation is stored in database 106 at 712. If the cardiologist logs into the Cardiologist Evaluation module 700 using a terminal that does not have a fingerprint scanner attached thereto, the cardiologist can enter a secure Personal Identification Number (PIN) to certify the results.

After a cardiologist has certified an ECG evaluation, the evaluation is eligible for quality review through the Quality Assurance module 1100. The ECGs are identified in the quality assurance queue of the Quality Assurance module 1100 according to a predefined set of rules. For example, a particular percentage, such as 2%, of all ECGs may be selected for quality assurance, along with each ECG associated with digital evaluation data representative of an evaluation indicating that an abnormality in an interval or intervals is present. The intervals measured for the marked heartbeats of ECGs selected for quality assurance by the Quality Assurance module 1100 are then re-measured using the process described above in connection with the IDM module 600. The ECG is then posted to the queue of a reviewing cardiologist for re-evaluation in Cardiologist Evaluation module 700.

The Reporting and Alerting module 900 automatically reports certified evaluations and results to sponsors and/or study sites by either electronic mail or facsimile. In the facsimile example, a facsimile server sends the report to a fax machine identified for a study site or sponsor. Additional reporting to the sponsor may include a digital file including the annotated image of the ECG, the measurement data and the cardiologist evaluation data. The reporting occurs in a form and at a time dictated by digital parameter data established in the initial trial setup using Trial Setup module 200. For example, reporting may occur on an individual ECG or group of ECGs basis daily, weekly or monthly, or be based upon the number of evaluated and certified ECG evaluations.

A portion of the functionality of the Reporting and Alerting Module 900 is dedicated to alerting a sponsor and/or Study site when predefined conditions are detected by an ECG interval duration measurement. For example, some sponsors prefer to be notified immediately when an Interval measurement falls outside of a predetermined time range. An interval measurement outside of this range may identify a potentially dangerous heart condition. An electronic mail or facsimile is automatically generated by the Reporting and Alerting module 900 after the measurement data are released from the IDM module 600 to data storage unit 106, with an indication that the data are only preliminary results that have not been evaluated by a cardiologist or quality controlled. Alerts can also be generated based upon negative (e.g., medically alarming) evaluation data in a certified evaluation report prior to a predefined reporting period if the sponsor so desires.

A sponsor or a study site representative may access the system using Sponsor/Study Site Access module 1000. This module allows the sponsor to reconfigure reporting options and formats and contact information, as well as trial parameters, such as protocols governing the number of intervals that must be measured for each ECG tracing and alerting parameters. Of course, precaution should be taken to ensure that only authorized personnel have access to this module, such as through usernames and passwords and encryption/key software, as should be familiar to those of ordinary skill.

The system preferably maintains a complete audit trail in database 106 of users that make data entries and particularly data changes. User names and dates are preferably associated with each entry and change. Changes to data entered into the system may also require a certification as described above. These features help ensure that the data accumulated by the system meet regulatory standards. The audit data are stored in database 106 and are activated as needed.

In one embodiment, in addition to reporting evaluation results to study sites and sponsors, accumulated data, particularly interval duration measurement data, demographic data, digital ECG data, digital annotation data and/or digital evaluation data are directly accessible by a regulatory agency such as the FDA or CPMP. A standard for this data has been proposed and may be reviewed at the FDA website at www.FDA.gov/cder/regulatory/ersr/ecgpresentations.htm (visited Nov. 20, 2001). Once a standard is established, the data may be provided directly to an agency via storage mediums such as CD ROMs or uploaded through a network such as Internet 114 to an agency processor 104 remote from processor 104 of the ECG processing company or a processor of the sponsor. Alternatively, the agency may be provided access through a Web page interface to the data in the database 106. In still another embodiment, this data may be provided to the sponsor in an appropriate digital format for reporting to the regulatory agency by the sponsor.

The present invention can be embodied in the form of methods and apparatus for practicing those methods. The present invention can also be embodied in the form of program code embodied in tangible media, such as floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

Although exemplary embodiments are described in detail above, the invention is not limited thereto. Rather, the invention should be construed broadly to include other variants and embodiments, which may be practiced within the scope and range of equivalents of the appended claims.

What is claimed is:

1. A method of processing an electrocardiogram (ECG), comprising the steps of:
   receiving digital ECG data, said digital ECG data evincing a plurality of a patient's heartbeats detected during an ECG;
   generating digital annotation data, said digital annotation data representing markings to be shown on an ECG tracing image of said plurality of heartbeats;
   generating digital interval duration data representing a time duration of an interval associated with an interval duration measurement, said generating step including the steps of:
      displaying said ECG tracing image of said plurality of heartbeats on a display of a user terminal;
      identifying endpoints of said interval; and
      determining said time duration of a measured interval based at least in part on said identified endpoints, wherein said markings identify at least one heartbeat from said plurality of heartbeats associated with said interval duration measurement; and
   developing an annotated ECG tracing image using said digital ECG data and said digital annotation data.

2. The method of claim 1, wherein the step of developing said annotated ECG tracing image includes the step of displaying said annotated ECG tracing imago on a display of a user terminal.

3. The method of claim 1, wherein said markings identify said endpoints.

4. The method of claim 1, wherein said markings further identify a time duration of said measured interval.

5. The method of claim 1, wherein said digital ECG data evince an image of an ECG tracing.

6. The method of claim 1, further comprising the step of receiving digital demographic data associated with said patient and said ECG.

7. The method of claim 1, further comprising the steps of:
   displaying said annotated ECG image on a display of a user terminal to an evaluating physician;
   providing said evaluating physician with interval duration data, said interval duration data developed from said digital interval duration data; and
   receiving digital evaluation data representing a medical evaluation of said ECG by said evaluating physician.

8. The method of claim 7, wherein said digital evaluation data are received by a computer processor unit through a computer network from a user terminal remote from said computer processor unit.

9. The method of claim 7, further comprising the steps of:
   displaying a second annotated ECG image on a display of a user terminal to said evaluating physician, said second annotated ECG image being associated with a prior ECG of said patient; and
   providing said evaluating physician interval duration data and evaluation data associated with said second annotated ECG image, said interval duration data and evaluation data being developed from digital interval duration data and digital evaluation data.

10. The method of claim 7, wherein digital evaluation data are received for a plurality of ECGs for a plurality of patients within a clinical study, the method further comprising the step of:
    automatically identifying at least one ECG from said plurality of ECGs for quality review based at least in part on digital evaluation data or digital interval duration data associated with said plurality of ECGs.

11. The method of claim 7, wherein digital evaluation data are received for a plurality of ECGs for a plurality of patients within a clinical study, the method further comprising the steps of:
    automatically generating a report for at least one ECG from said plurality of ECGs, said report including evaluation data developed from digital evaluation data associated with said at least one ECG from said plurality of ECGs; and automatically providing said report to a party identified by digital reporting criteria for said clinical study and in a manner identified by said digital reporting criteria.

12. The method of claim 1, wherein said digital ECG data and digital annotation data are provided to a regulatory agency processor through a computer network from a computer processor unit remote from said regulatory agency processor.

13. The method of claim 12, wherein said computer network is the Internet.

14. An electrocardiogram (ECG) processing system, comprising:
    at least one processor, said at least one processor configured to:
       generate digital annotation data, said digital annotation data representing markings to be shown on an ECG tracing image of a plurality of a patient's heartbeats detected during art ECG, wherein said marking identify at least one heartbeat from said plurality of heartbeats associated with an interval duration measurement;
       generate digital interval duration data, said digital interval duration data representing a time duration of an interval associated with said interval duration measurement;

display said ECG tracing image on a display;

receive endpoint data representing identified endpoints of said interval;

generate said digital interval duration data at least in part from said endpoint data; and develop an annotated ECG tracing image using said digital annotation data and digital ECG data, said digital ECG data evincing said plurality of a patient's heartbeats.

15. The system of claim 14, further comprising:

at least one receiving station for receiving said digital ECG data from at least one ECG machine, said at least one processor being further configured to receive said digital ECG data from said receiving station.

16. The system of claim 15, wherein:

said receiving station receives digital demographic data associated with said patient and said ECG, and said at least one processor is configured to receive said digital demographic data from said receiving station.

17. The system of claim 14, further comprising a display for displaying said annotated ECG tracing image.

18. The system of claim 14, wherein said markings identify said endpoints.

19. The system of claim 18, wherein said marking further identify a time duration of said measured interval.

20. The system of claim 14, comprising a display for displaying said annotated ECG image to an evaluating physician and for displaying interval duration data developed from said digital interval duration data, said at least one processor further configured to receive digital evaluation data representing a medical evaluation of said ECG by said evaluating physician.

21. The system of claim 20, further comprising a Computer processor unit remote from said at least one processor for providing said digital evaluation data to said at least one processor unit through a computer network.

22. The system of claim 21, wherein said computer network is the Internet.

23. The system of claim 20, wherein a second annotated ECG image is displayed to said evaluating physician on said display, said second annotated ECG image being associated with a prior ECG of said patient and wherein said at least one processor is configured to provide interval duration data and evaluation data associated with said second annotated ECG image to said evaluating physician on said display.

24. The system of claim 20, wherein digital evaluation data are received by said at least one processor for a plurality of ECGs for a plurality of patients within a clinical study, said at least one processor automatically identifies at least one ECG from said plurality of ECGs for quality review based at least in part on digital evaluation data or digital interval duration data associated with said plurality of ECGs.

25. The system of claim 20, wherein:

digital evaluation data are received by said at least one processor for a plurality of ECGs for a plurality of patients within a clinical study, and said at least one processor is configured to:

automatically generate a report for at least one ECG from said plurality of ECGs, said report including evaluation data developed from digital evaluation data received for said at least one ECG; and automatically provide said report to a party identified by digital reporting criteria for said clinical study and in a manner identified by said digital reporting data.

26. The system of claim 14, wherein said at least one processor is configured to provide said digital ECG data and digital annotation data to a regulatory agency processor remote from said at least one processor through a computer network.

27. A method of processing an electrocardiogram (ECG), comprising the steps of:

receiving digital parameter data clinical study, digital parameter data representing demographic data to be collected for ECGs associated with said clinical study, rules associated with said clinical study and query resolution contact information;

receiving digital demographic data evincing demographic data for an ECG associated with said clinical study; and automatically generating a query in accordance with said query resolution contact information if a problem is identified with said demographic data based upon said digital parameter data.

28. The method of claim 27, wherein said step of automatically generating said query includes the step of identifying whether demographic data are missing, said demographic data violate a rule associated with said clinical study, said demographic data are inconsistent with demographic data evinced by digital demographic data received for a second ECG associated with said clinical study, or a combination thereof.

29. The method of claim 27, wherein said query resolution contact information includes an identification of a party to be contacted and a contact method.

30. The method of claim 27, further comprising the steps of:

displaying an ECG image on a display of a user terminal to an evaluating physician, said ECG image developed from digital ECG data, said digital ECG data evincing a plurality of a patient's heartbeats detected during an ECG;

providing said evaluating physician with interval duration data, said interval duration data developed from digital interval duration data representing a time duration of a measured interval associated with at least one heartbeat from said plurality of heartbeats; and receiving digital evaluation data representing a medical evaluation of said ECG by said evaluating physician.

31. The method of claim 30, wherein said digital evaluation data are received by a computer processor unit through a computer network from a user terminal remote from said computer processor unit.

32. The method of claim 30, further comprising the steps of:

displaying a second annotated ECG image on a display of a user terminal to said evaluating physician, said second annotated ECG image being associated with a prior ECG of said patient; and providing said evaluating physician interval duration data and evaluation data associated with said second annotated ECG image, said interval duration data and evaluation data being developed from digital interval duration data and digital evaluation data.

33. The method of claim 30, wherein said digital parameter data represent quality review rules, and wherein digital evaluation data are received for a plurality of ECGs for a plurality of patients within said clinical study, the method further comprising the step of:

automatically identifying at least one ECG from said plurality of ECGs for quality review based at least in part on said digital parameter data.

34. The method of claim 33, wherein said automatically identifying step includes the step of identifying at least one ECG for quality review based at least in part on digital evaluation data received for said plurality of ECGs or digital interval duration data associated with said plurality of ECGs.

35. The method of claim 30,
wherein said digital parameter data represent reporting rules, and
wherein digital evaluation data are received for a plurality of ECGs for a plurality of patients within said clinical study, the method further comprising the steps of:
automatically generating a report for at least one ECG from said plurality of ECGs, said report including evaluation data developed from respective digital evaluation data for said at least one ECG; and
automatically providing said report to a party identified by said digital parameter data for said clinical study and in a manner identified by said digital parameter data.

36. An electrocardiogram (ECG) processing system, comprising:
at least one processor, said at least one processor configured to:
receive digital parameter data for a clinical study, said digital parameter data representing demographic data to be collected for ECGs associated with said clinical study, rules associated with said clinical study and query resolution contact information;
receive digital demographic data evincing demographic data for an ECG associated with said clinical study; and automatically generate a query in accordance with said query resolution contact information if a problem is identified with said demographic data based upon said digital parameter data.

37. The system of claim 36, wherein said at least one processor is configured to automatically generate said query by identifying whether demographic data are missing, said demographic data violate a rule associated with said clinical study, said demographic data are inconsistent with demographic data evinced by digital demographic data received for a second ECG associated with said clinical study, or a combination thereof.

38. The system of claim 36, wherein said query resolution contact information includes an identification of a party to be contacted and a contact method.

39. The system of claim 36, further comprising:
a display for displaying an ECG image to an evaluating physician, said ECG image developed from digital ECG data, said digital ECG data evincing a plurality of a patient's heartbeats detected during an ECG, and for displaying interval duration data, said interval duration data developed from digital interval duration data representing a time duration of a measured interval associated with at least one heartbeat from said plurality of heartbeats,
wherein said at least one processor is configured to receives digital evaluation data representing a medical evaluation of said ECG by said evaluating physician.

40. The system of claim 39, wherein said digital evaluation data are received through a computer network from a user terminal remote from said at least one processor.

41. The system of claim 39,
wherein said display displays a second annotated ECG image to said evaluating physician, said second annotated ECG image being associated with a prior ECG, and
wherein said at least one processor is configured to provide interval duration data and evaluation data associated with said second annotated ECG image to said display for display to said evaluating physician.

42. The system of claim 39,
wherein said digital parameter data represent quality review rules,
wherein said digital evaluation data are received by said at least one processor for a plurality of ECGs for a plurality of patients within said clinical study, and
wherein said at least one processor is configured to automatically identify at least one ECG from said plurality of ECGs for quality review based at least in part on said digital parameter data.

43. The system of claim 42, wherein said at least one processor is configured to automatically identify said at least one FCC based at least in part on digital evaluation data received for said plurality of ECGs or digital interval duration data associated with said plurality of ECGs.

44. The system of claim 39,
wherein said digital parameter data represent reporting rules, and
wherein said digital evaluation data are received for a plurality of ECGs for a plurality of patients within said clinical study,
said at least one processor being further configured to:
automatically generate a report for at least one ECG from said plurality of ECGs, said report including evaluation data developed from respective digital evaluation data for said at least one ECG, and
automatically provide said report to a parry identified by said digital parameter data for said clinical study and in a manner identified by said digital parameter data.

45. A method of processing an electrocardiogram, comprising the a steps of:
receiving digital ECG data, said digital ECG data evincing a plurality of a patient's heartbeats detected during an ECG;
generating digital annotation data, said digital annotation data representing markings to be shown on an ECG tracing image of said plurality of heartbeats;
developing an annotated ECG tracing image using said digital ECG data and said digital annotation data;
displaying said annotated ECG image on a display of a user terminal to an evaluating physician;
providing said evaluating physician with interval duration data, said interval duration data developed from digital interval duration data representing a time duration of a measured interval associated with at least one heartbeat from said plurality of heartbeats; and
receiving digital evaluation data representing a medical evaluation of said ECG by said evaluating physician,
wherein digital evaluation data are received for a plurality of ECGs for a plurality of patients within a clinical study, the method further comprising the step of:
automatically identifying at least one ECG from said plurality of ECGs for quality review based at least in part on digital evaluation data or digital interval duration data associated with said plurality of ECGs.

46. A method of processing an electrocardiogram, comprising the steps of:
receiving digital ECG data, said digital ECG data evincing a plurality of a patient's heartbeats detected during an ECG;

generating digital annotation data, said digital annotation data representing markings to be shown on an ECG tracing image of said plurality of heartbeats;

developing an annotated ECG tracing image using said digital ECG data and said digital annotation data;

displaying said annotated ECG image on a display of a user terminal to an evaluating physician;

providing said evaluating physician with interval duration data, said interval duration data developed from digital interval duration data representing a time duration of a measured interval associated with at least one heartbeat from said plurality of heartbeats; and receiving digital evaluation data representing a medical evaluation of said ECG by said evaluating physician, wherein digital evaluation data are received for a plurality of ECGs for a plurality of patients within a clinical study, the method further comprising the steps of:

automatically generating a report for at least one ECG from said plurality of ECGs, said report including evaluation data developed from digital evaluation data associated wit said at least one ECG from said plurality of ECGs; and automatically providing said report to a party identified by digital reporting criteria for said clinical study and in a manner identified by said digital reporting criteria.

47. A method of processing an electrocardiogram (ECG), comprising the steps of:

receiving digital ECG data, said digital ECG data evincing a plurality of a patient's heartbeats detected during an ECG;

generating digital annotation data, said digital annotation data representing markings to be shown on an ECG tracing image of said plurality of heartbeats; and developing an annotated ECG tracing image using said digital ECG data and said digital annotation data, wherein said digital ECG data and digital annotation data are provided to a regulatory agency processor through a computer network from a computer processor unit remote from said regulatory agency processor.

48. The method of claim 47, wherein said computer network is the Internet.

49. An electrocardiogram (ECG) processing system, comprising:

at least one processor, said at least one processor configured to:

generate digital annotation data, said digital annotation data representing markings to be shown on an ECG tracing image of a plurality of a patient's heartbeats detected during and ECG; and develop an annotated ECG tracing image using said digital annotation data and digital ECG data, said digital ECG data evincing said plurality of a patient's heartbeats; and a display for displaying said annotated ECG image to an evaluating physician and for displaying interval duration data developed item digital interval duration data representing a time duration of a measured interval associated with at least one heartbeat from said plurality of heartbeats, said at least one processor further configured to receive digital evaluation data representing a medical evaluation of said ECG by said evaluating physician, wherein digital evaluation data are received by said at least one processor for a plurality of ECGs for a plurality of patients within a clinical study, said at least one processor further configured to automatically identify at least one ECG from said plurality of ECGs for quality review based at least in part on digital evaluation data or digital interval duration data associated with said plurality of ECGs.

50. An electrocardiogram (ECG) processing system, comprising:

at least one processor, said at least one processor configured to:

generate digital annotation data, said digital annotation data representing markings to be shown on an ECG tracing image of a plurality of a patient's heartbeats detected during and ECG; and develop an annotated ECG tracing image using said digital annotation data and digital ECG data, said digital ECG data evincing said plurality of a patient's heartbeats; and a display for displaying said annotated ECG image to an evaluating physician and for displaying interval duration data developed from digital interval duration data representing a time duration of a measured interval associated with at least one heartbeat from said plurality of heartbeats, said at least one processor further configured to receive digital evaluation data representing a medical evaluation of said ECG by said evaluating physician, wherein:

digital evaluation data are received by said at least one processor for a plurality of ECGs for a plurality of patients within a clinical study, and said at least one processor is further configured to:

automatically generate a report for at least one ECG from said plurality of ECGs, said report including evaluation data developed from digital evaluation data received for said at least one ECG; and automatically provide said report to a party identified by digital reporting criteria for said clinical study and in a manner identified by said digital reporting data.

51. An electrocardiogram (ECG) processing system, comprising:

at least one processor, said at least one processor configured to:

generate digital annotation data, said digital annotation data representing markings to be shown on an ECG tracing image of a plurality of a patient's heartbeats detected during an ECG;

develop an annotated ECG tracing image using said digital annotation data and digital ECG data, said digital ECG data evincing said plurality of a patient's heartbeats; and provide said digital ECG data and digital annotation data to a regulatory agency processor remote from said at least one processor through a computer network.

52. The system of claim 51, wherein said computer network is the Internet.

53. An electrocardiogram (ECG) processing system, comprising:

at least one processor, said at least one processor configured to:

generate digital annotation data, said digital annotation data representing markings to be shown on an ECG tracing image of a plurality of a patient's heartbeats detected during an ECG;

develop an annotated ECG tracing image using said digital annotation data and digital ECG data, said digital ECG data evincing said plurality of a patient's heartbeats;

receive said digital ECG data from a receiving station; and receive digital demographic data from said receiving station.

54. The system of claim 53, further comprising at least one receiving station for receiving said digital ECG data from at least one ECG machine.

55. A method of processing an electrocardiogram (ECG), comprising the steps of:

receiving digital ECG data from a receiving station, said digital ECG data evincing a plurality of a patient's heartbeats detected during an ECG;

generating digital annotation data, said digital annotation data representing markings to be shown on an ECG tracing image of said plurality of heartbeats;

developing an annotated ECG tracing image using said digital ECG data and said digital annotation date; and receiving digital demographic data associated with said patient and said ECG from said receiving station.

56. The method of claim 55, wherein said receiving station receives said digital ECG data from at least one ECG machine.

* * * * *

UNITED STATES PATENT AND TRADEMARK OFFICE
CERTIFICATE OF CORRECTION

PATENT NO. : 6,708,057 B2
DATED : March 16, 2004
INVENTOR(S) : Joel Morganroth

It is certified that error appears in the above-identified patent and that said Letters Patent is hereby corrected as shown below:

Column 15,
Line 60, delete "imago" and insert therefor -- image --;

Column 16,
Line 60, delete "art" and insert therefor -- an --;

Column 18,
Line 8, insert -- for a -- after the word "data";
Line 8, insert -- said -- after the word "study,";

Column 20,
Line 17, delete "FCC" and insert therefor -- ECG --;
Line 31, delete "parry" and insert therefor -- party --;

Column 21,
Line 21, delete "wit" and insert therefor -- with --;
Line 59, delete "item" and insert therefor -- from --; and Column 24,
Line 5, delete "date" and insert therefor -- data --.

Signed and Sealed this

Thirtieth Day of August, 2005

JON W. DUDAS
*Director of the United States Patent and Trademark Office*